(12) United States Patent
Akao et al.

(10) Patent No.: US 8,174,689 B2
(45) Date of Patent: May 8, 2012

(54) APPARATUS FOR INSPECTING DEFECTS OF HONEYCOMB STRUCTURE

(75) Inventors: Takayoshi Akao, Nagoya (JP); Hiroyuki Shindo, Kasugai (JP); Jun Inoue, Aichi-prefecture (JP); Keita Oikawa, Nagoya (JP)

(73) Assignee: NGK Insulators, Ltd., Nagoya (JP)

( * ) Notice: Subject to any disclaimer, the term of this patent is extended or adjusted under 35 U.S.C. 154(b) by 546 days.

(21) Appl. No.: 12/403,599

(22) Filed: Mar. 13, 2009

(65) Prior Publication Data
US 2009/0237652 A1 Sep. 24, 2009

(30) Foreign Application Priority Data

Mar. 21, 2008 (JP) .................................. 2008-073017
Mar. 11, 2009 (JP) .................................. 2009-058746

(51) Int. Cl.
*B01D 46/00* (2006.01)
*G01N 21/00* (2006.01)

(52) U.S. Cl. ......... 356/237.1; 356/437; 95/279; 95/273; 55/523; 73/114.31; 73/114.35; 73/52; 436/164

(58) Field of Classification Search ............... 356/237.1; 55/523; 95/279, 273
See application file for complete search history.

(56) References Cited

U.S. PATENT DOCUMENTS

| | | |
|---|---|---|
| 2002/0197193 A1 | 12/2002 | Harada et al. |
| 2003/0048941 A1 | 3/2003 | Minami |
| 2003/0112437 A1 | 6/2003 | Enomoto et al. |
| 2003/0174320 A1 | 9/2003 | Yokoyama et al. |
| 2007/0022724 A1* | 2/2007 | Gargano et al. ................. 55/523 |
| 2007/0238191 A1 | 10/2007 | Gargano et al. |
| 2009/0051909 A1 | 2/2009 | Kato |

FOREIGN PATENT DOCUMENTS

| | | |
|---|---|---|
| EP | 1 296 125 A1 | 3/2003 |
| EP | 2 031 378 A1 | 3/2009 |
| JP | 2001-190916 A1 | 7/2001 |
| JP | 3904933 B2 | 4/2007 |
| WO | 2007/111014 A1 | 10/2007 |

* cited by examiner

*Primary Examiner* — Gregory J Toatley
*Assistant Examiner* — Rebecca C Slomski
(74) *Attorney, Agent, or Firm* — Burr & Brown

(57) ABSTRACT

According to an apparatus for inspecting defects of a honeycomb structure that is provided with a current plate and an air current formation means (air source and a header tube), fine defects or defects taking place in the vicinity of an outer periphery of the honeycomb structure can be detected with high sensitivity.

7 Claims, 3 Drawing Sheets

APPARATUS FOR INSPECTING DEFECTS OF HONEYCOMB STRUCTURE

FIELD OF THE INVENTION

The present invention relates to an apparatus for use in inspecting a honeycomb structure for the presence or the absence of pores (defects) that are larger than the diameter of a pore of a honeycomb structure where defects are not present in a normal honeycomb structure.

BACKGROUND OF THE INVENTION

In consideration of environmental influences, there has been a higher need of removing granular substances that are contained in an exhaust gas to be exhausted from an automobile engine or the like from the exhaust gas. In particular, the regulation regarding the removal of granular substances (particulate matters (PM)) to be discharged from a diesel engine tends to be more strict globally. Under such situations, a diesel particulate filter (DPF) for collecting and removing PM attracts attention.

As a mode of a DPF, there is proposed a filter (honeycomb filter) having a plugged honeycomb structure. This honeycomb filter is formed of a honeycomb structure in which there is provided a porous partition wall of defining and forming a plurality of cells acting as through channels of a fluid, having predetermined cells in which one end portion is open and the other end portion is plugged and remaining cells in which one end portion is plugged and the other end portion is open, the predetermined cells and remaining cells being alternately located. According to this type of honeycomb filter, a fluid (exhaust gas) flowing in the open one end portion of the predetermined cells, penetrating the partition wall, flowing out to the side of the remaining cells as a penetrated fluid, and then flowing out from the open other end portion of the remaining cells, thereby enabling the honeycomb filter to collect and remove PM in the fluid (exhaust gas).

In the above-mentioned honeycomb filter, the honeycomb filter has a structure in which an exhaust gas penetrates a porous partition wall (honeycomb filter of wall flow type) and, due to a large filtration area, the velocity of filtration (the velocity of penetration of the exhaust gas through the partition wall) is decreased and the pressure drop is small, as well as the collection efficiency of PM is comparatively good. However, these advantages are provided based on the assumption that in the porous partition wall of the honeycomb structure forming the honeycomb filter, there are no unintended pores larger than the pore diameter of the honeycomb structure (defects). In case of the presence of defects, PM passes therethrough before PM can be efficiently collected and the PM collection performance as a DPF is reduced. Therefore, an inspection for defects during the manufacturing of the honeycomb structure is a very important process. Incidentally, as a related prior art document, Patent Document 1 (Japanese Patent No. 3904933) can be proposed.

SUMMARY OF THE INVENTION

In Patent Document 1, a means of detecting with high sensitivity defects of a honeycomb structure of such a configuration that defects cannot be externally confirmed is disclosed. In Patent Document 1, however, in the case where defects are so small as to be about 10 times the average pore diameter of a honeycomb structure, are not significantly larger than a normal pore, or in the case where defects are present in the vicinity of the outer periphery of the honeycomb structure, it is found that there is a possibility of the reduction of sensitivity for detecting the defects in the honeycomb structure.

The present invention has been made in view of such situations, and has an object of providing means that can detect with high sensitivity small defects and defects taking place in the vicinity of an outer periphery of a honeycomb structure. To solve such problems, as a result, amounts of study leads to consideration of the following means.

That is, first, according to the present invention, provided is an apparatus for inspecting defects of a honeycomb structure, comprising:

a fine grain introduction means of pressurizing a gas containing a fine grain to introduce the fine grain into a cell from one face (fine grain introduction face) side of a honeycomb structure;

a fine grain-containing gas flow control means of controlling a flow of this gas to be introduced;

a light application means of applying a light of high directivity so as to pass in parallel in the vicinity of the other face (fine grain discharge face) of the honeycomb structure;

a current plate disposed so as to cover the other face (fine grain discharge face) of the honeycomb structure between a light emitted from this light application means and the other face (fine grain discharge face) of the honeycomb structure; and an air current formation means causing a gas to flow along an outer periphery of the honeycomb structure in a direction from one face (fine grain introduction face) side toward the other face (fine grain discharge face) side of the honeycomb structure.

A honeycomb structure, being a body to be inspected of an apparatus for inspecting defects of a honeycomb structure according to the present invention is a porous body which includes one face (fine grain introduction face) and the other face (fine grain discharge face), which is provided with a porous partition wall defining and forming a plurality of cells acting as through channels of a fluid providing a connection therebetween, and in which predetermined cells are open on one face (fine grain introduction face) side and plugged on the other face (fine grain discharge face) side, and the remaining cells are plugged at one face (fine grain introduction face) side and open at the other face (fine grain discharge face) side, are alternately disposed. Insofar as the one in which defects may take place, there is no limit to the shape, material, pore diameter, application and the like.

Furthermore, it is preferable that a body to be inspected is a honeycomb structure having a segment structure that is preferably employed in a DPF (for example, a honeycomb structure disclosed in Patent Document 2 (JP-A-2001-190916). This is the one in which a plurality of honeycomb segments are bonded via a bonding layer. A current plate effectively acts, as the bonding layer, even with respect to the portion where the pattern regularity of the arrangement of cells is impaired, and an air current containing fine grains may be turbulent.

In the apparatus for inspecting defects of a honeycomb structure according to the present invention, a light application means can be formed of, for example, a light generation means and a lens.

The light to be applied by the light application means needs to be a light having a wavelength that is scattered by fine grains. In this respect, the light is preferably a laser beam. Preferred usable examples include a solid laser, a gas laser, a semi-conductor laser, a dye laser, an excimer laser, and a free electron laser. The wavelength of the light employed can be, for example, about 650 nm (red laser beam), about 532 nm (green laser beam), about 400 nm (purple laser beam) and the like. Further, it is desired to readily detect this scattered light.

In addition, the light is made to pass in an extent preferably up to 30 mm from right above the other face (fine grain discharge face), more preferably up to 10 mm from right above the other face (fine grain discharge face). This reason is that the reduction of sensitivity due to prevent diffusion of fine grains that have been discharged from the other face (fine grain discharger face). It is desired that alight is applied in a planar way. For example, the light application means is provided with a lens, whereby a generated light can be diffused and applied in a planar way. Furthermore, by scanning the light application means itself, a light can be diffused and applied in a planar way as well.

In the apparatus for inspecting defects of a honeycomb structure according to the present invention, as the method of generating fine grains to be contained in a gas containing fine grains, one of the following exemplary methods can be employed, a method of burning incenses such as an incense stick, a method of atomizing glycols or water to generate fine grains, a method of generating fine grains of water using a solid carbon dioxide, a liquid nitride, an atomizer, an ultrasonic humidifier and the like, a method of using a commercially available standard grain generator, a method of raising dust of fine grain powders of e.g., calcium carbonate using a vibration apparatus, a blower or the like.

The grain diameter of fine grains can be selected as appropriate depending on the configuration, the pore diameter and the like of a honeycomb structure. In addition, by examining the relationship between the kind of defects and the grain size distribution of fine grains to be discharged, the grain diameter suitable to a honeycomb structure, being a body to be inspected can be selected. When the grain diameter is too large, the amount to be collected in pores of the honeycomb structure, being a porous body is too large, and thus the need of removal thereof by after treatment arises. When the grain diameter is too small, the difference in the amount of fine grains to be discharged depending on the presence or the absence of defects is unlikely to appear, and the sensitivity may be decreased. The grain diameter is preferably 0.3 µm to 200 µm, more preferably 0.5 µm to 50 µm, still more preferably 1 µm to 10 µm. However, even if fine grains having the grain diameter out of the above-mentioned range are contained in fine grains to be generated, fine grains in the above-mentioned range have only to be contained at such an amount that an object of the present invention can be achieved.

As a fine grain introduction means, for example, the method in which a gas containing fine grains is stored in a limited space (grain chamber) thereafter to be at a predetermined concentration can be employed, and then by the application of a predetermined pressure from the fine grain introduction face side of the honeycomb structure, introduced into the cells of the honeycomb structure. In this method a duct is disposed above the fine grain discharge face of the honeycomb structure and an air is exhausted using e.g., a fan, and a gas containing fine grains is sucked from the fine grain discharge face side and introduced into the cells of the honeycomb structure, or the like.

A fine grain-containing gas flow control means, for example, in the case in which a gas containing fine grains is stored in the grain chamber, can employ a regulator that is mounted at, for example, a compressor acting to apply pressure in this grain chamber and that regulates its pressure. In case where a pressure is regulated, the flow is controlled.

An applied pressure of a gas containing fine grains can be properly selected in accordance with the configuration or the like of a honeycomb structure, being a body to be inspected.

In the case in which the porosity of the honeycomb structure is high, the pressure drop of the honeycomb structure is small, an air current of the gas containing fine grains can be formed by a small applied pressure, and thus defects can be detected. On the other hand, when the porosity of the honeycomb structure is low, the pressure drop of the honeycomb structure is large, and a large applied pressure is required. When an applied pressure is too small with respect to an appropriate applied pressure, an air current is not stable, and defects may not be specified. In addition, as an applied pressure is increased, the distance of fine grains to be discharged from the honeycomb structure flowing in a laminar flow comes to be long, and detection can be made even if a light is made to pass apart from the honeycomb structure. Too large applied pressure is not desired because due to that a large amount of fine grains flow out through the honeycomb structure (partition wall), being a porous body, fine grains to be discharged from fine defects cannot be detected, or more amounts of fine grains are needed.

The concentration of fine grains in a gas containing fine grains can select as appropriate a concentration of fine grains at which concentration can be detected by a light of high directivity, being such a concentration that the contrast between the portion of detects and the other portions is sharp.

In the apparatus for inspecting defects of a honeycomb structure according to the present invention, an air current formation means can include, for example, a header tube having a nozzle or a pore from which a gas such as air can be blown out, a compressor acting as an air source, and a piping providing a connection therebetween. Furthermore, it is preferable to employ means of disposing a heater and generating an ascending air current by the air that is heated by the heater. It is preferable that the air current generation means is means of forming an air current toward the side face (peripheral surface) of the honeycomb structure from a position apart therefrom. A preferred air current formation means is as follows.

In an apparatus for inspecting defects of a honeycomb structure according to the present invention, it is preferable that the air current formation means includes a plurality of nozzles blowing out a gas.

In an apparatus for inspecting defects of a honeycomb structure according to the present invention, it is preferable that there are provided an air current formation gas pressurizing means of pressurizing a gas that is made to flow by the air current formation means, and an air current formation gas flow control means of controlling a flow of a gas that is made to flow by the air current formation means.

An air current formation gas pressurizing means, for example, in the case of using a compressor as an air current formation means, can include a regulator that is mounted at this compressor. An air current formation gas flow control means, for example, in the case in which an air current formation means is formed of a header tube, a compressor and a piping, can include a flow control valve that is mounted at this piping.

In the apparatus for inspecting defects of a honeycomb structure according to the present invention, a current plate is a member having an opening with respect to the flow direction of a gas containing fine grains, and preferably employs a plate member having a number of pores or a mesh-like member. Most of all, it is desired to use a screen into which fibers of metal, resin, cotton, silk or the like are woven. The shape of an open frontal area can employ e.g., a triangular, quadrilateral, hexagonal shape. The pitch of an opening is preferably smaller than a cell pitch of a honeycomb structure, more preferably not more than ½ the cell pitch, still more preferably not more than ¼ the cell pitch. The diameter of the opening can be properly selected depending on the position, the size or the like of a cell to be formed in the honeycomb structure, but preferably 5 μm to 2000 μm, more preferably 30 μm to 500 μm. When it is not more than 5 μm, there is a possibility that fine grains are adhered and collected. When it is not less than 2000 μm, there is a possibility that improved effects by current straightening cannot be obtained. The thickness of the current plate is selected as appropriate depending on the distance of an opening forming the current plate with respect to an adjacent opening, but preferably not more than 1 mm, most preferably 5 μm to 300 μm. When this thickness exceeds 1 mm, there is a possibility that fine grains are adhered and collected by the current plate. A current plate which surface is coated with a black color, plated or applied with non-gloss treatment is preferably used. This reason is to be able to reduce the possibility that by the reflection and scattering of a laser light on the surface of the current plate, defects becomes hard to be detected.

In an apparatus for inspecting defects of a honeycomb structure according to the present invention, it is preferable that a distance between the current plate and the other face (fine grain discharge face) of the honeycomb structure is not less than 0.01 mm to not more than 30 mm.

The above-mentioned distance is more preferably not less than 0.1 mm to not more than 10 mm, most preferably not less than 0.1 mm to not more than 5 mm.

In an apparatus for inspecting defects of a honeycomb structure according to the present invention, it is preferable that the current plate is not less than 10% to not more than 80% in its open area ratio.

In an apparatus for inspecting defects of a honeycomb structure according to the present invention, it is preferable that there is provided an observation means of observing the light scattered by the fine grain from a position forming an angle with respect to a direction of a normal to the other face (fine grain discharge face) of the honeycomb structure. In this case, it is preferable that the observation means is means of taking an image of the other face (fine grain discharge face) of the honeycomb structure using a camera.

The above-mentioned camera preferably employs an optical video camera, a camera, a digital camera using a solid imaging element or the like.

The angle with respect to the direction of the normal to the other face (fine grain discharge face) of the other face of the above-mentioned honeycomb structure is preferably not less than 10 degrees to not more than 80 degrees. It is more preferably not less than 30 degrees to not more than 60 degrees. This reason is that when observed in a slanting direction, defects are easy to be detected. It is preferable that an observation means is a seeing other than a camera. It is preferable that there is provided in this direction an observation window.

The apparatus for inspecting defects of a honeycomb structure according to the present invention is provided with a current plate that is disposed between a light having been emitted from a light application means and the other face (fine grain discharge face) of the honeycomb structure, and an air current formation means of causing a gas to flow along the outer periphery of the honeycomb structure, so that even if defects are small or defects are present in the proximity of the outer periphery of the honeycomb structure, a highly sensitive detection can be made. This reason is that an air current ascending along the honeycomb structure passes through the current plate, thereby preventing an air current having passed through an internal part of the honeycomb structure from flowing with flows spread to the outside of the honeycomb structure or swinging to reduce a detection sensitivity.

Furthermore, it is superior in respect of no prevention of the observation in a slanting direction that a gas is made to flow along the outer periphery of the honeycomb structure (that an air current is formed). That is, for example, when an actual wall is disposed using a metal plate or a transparent resin, faults such as the restriction of a field of view or the change of an air current or the change of sensitivity owing to the adhesion of fine grains to the wall surface. With the use of the air current formation means, however, such problems can be avoided.

The formation of an air current by the suction from above (from the other face (fine grain discharge face) side of the honeycomb structure) can be made, but this method in which a current plate is disposed, an air current along the outer peripheral portion is formed, and a gas is pushed up from below (from one face (fine grain introduction face) side of the honeycomb structure) is superior in convenience of making defects visual and stability of an image.

The apparatus for inspecting defects of a honeycomb structure according to the present invention, in its preferred mode, due to that an air current formation means includes a plurality of nozzles blowing out a gas, is desired to inspect defects present in the vicinity of the outer periphery of the honeycomb structure because the direction of an air current can be regulated and a stable air current substantially at the same speed as is an air current passing through an internal part of the honeycomb structure can readily be generated. Furthermore, the direction of the nozzles is preferably substantially parallel with respect to the axis of the honeycomb structure, and the direction of the nozzles is more preferably the direction toward the proximity of the outer peripheral portion of the other face of the honeycomb structure. It is preferable that the direction of the nozzles is directed to the side face so as to from an ascending air current along the side face (peripheral surface) of the honeycomb structure. It is preferable that individual nozzles are pointed in a predetermined direction with respect to the axis, and that they are located, for example, with their directions alternately changed so as to include all the above-mentioned directions. In addition, it is preferable that the directions of nozzles are changed in each place in conformity with the configuration of the honeycomb structure. Most preferably, the direction of the nozzles, with respect to the axis of the honeycomb structure, is in the range from parallel (0 degrees) up to the direction inclined 30 degrees to the axis side from parallel. Even if there are plural kinds of the configuration or the size of a honeycomb structure, being a body to be inspected, it is unnecessary to change set-up every time. Further, even if the number of times of the change of set-ups is decreased, a stable air current can be formed.

In the apparatus for inspecting defects of a honeycomb structure according to the present invention, in its preferred mode, due to that there are provided an air current formation gas pressurizing means of pressurizing a gas that is made to flow by an air current formation means, and an air current formation gas flow control means of controlling the flow of a gas that is made to flow by an air current formation means, even in the case in which the flow of a gas containing fine grains is changed depending on the porosity, the pore diameter, the dimension or the like of the honeycomb structure, the optimum flow for detecting defects that are present in the vicinity of the outer periphery of the honeycomb structure can be obtained.

In the apparatus for inspecting defects of a honeycomb structure according to the present invention, in its preferred mode, due to that the distance between the current plate and the other face (fine grain discharge face) of the honeycomb structure is not less than 0.01 mm to not more than 30 mm, there are superior advantages of flow straitening with respect to a gas containing fine grains having penetrated the honeycomb structure, and the presence or the absence of small defects is easy to be determined and the place of these defects is easy to be specified. Even in the case in which the current plate and the honeycomb structure are brought in contact, advantages of flow straitening can be obtained. This case, however, is not desired because it causes the occurrence of defects such as the production of flaws and the adhesion of foreign substances to the honeycomb structure. Further, this case is not desired because also with respect to the current plate, it brings about flaws, deterioration, the adhesion of foreign substances and the like to be the cause of faults. In case where the distance therebetween is not less than 30 mm, there is a possibility that advantages of suppressing the diffusion of fine grains having been discharged from the cells of the honeycomb structure or the occurrence of a turbulent flow cannot be obtained.

In the apparatus for inspecting defects of a honeycomb structure according to the present invention, in its preferred mode, due to that the current plate is not less than 10% to not more than 80% in its open area ratio, fine grains just having penetrated the honeycomb structure is unlikely to diffuse, and the presence or the absence of small defects is easy to be determined and the place of these defects is easy to be specified. When the open area ratio is less than 10%, an air current is impaired, and there is a possibility that defects that could be seen in the case of no current plate cannot be seen. When the open area ratio is not less than 80%, there is a possibility that improved advantages of seeing of defects in the vicinity of the outer periphery cannot be obtained. More preferably, the open area ratio is not less than 10% to not more than 70%. By causing the open area ratio to be not more than 70%, great advantages of suppressing a reflected light form the other face of the honeycomb structure can be obtained, a contrast is improved, and defects can be easily seen wholly.

In the apparatus for inspecting defects of a honeycomb structure according to the present invention, in its preferred mode, due to that there is provided an observation means of observing the other face (fine grain discharge face) of the honeycomb structure from a position forming an angle with respect to the direction of the normal to the other face (fine grain discharge face) of the honeycomb structure, advantages of shielding a reflected light from the surface of the honeycomb structure (work) using the current plate are enhanced, resulting in improvements in detection sensitivity of defects. That is, although a light to be observed contains a scattered light (including defects information) from a gas containing fine grains having passed through the current plate and a reflected light from the surface of the honeycomb structure, when observed from a position having an angle, a reflected light from the surface of the honeycomb structure is decreased by the current plate, and thus defects are more likely to be seen. In addition, in the case of observation from right above the honeycomb structure, there is a possibility that an air current of a gas containing fine grains is disturbed by mounting a camera or by means of securing a field of view from an observation window, but such disadvantages can be avoided.

In the apparatus for inspecting defects of a honeycomb structure according to the present invention, in its preferred mode, due to that an observation means is means of taking an image of the other face (fine grain discharge face) of the honeycomb structure using a camera, so that information of defects is easy to be quantified, and information (of defects) having fluctuations such as scattered light from the gas containing fine grains can be added up timely and spatially, and averaged to be stable. Further, by this stabilization of information, fine defects can be defected with stability. Furthermore, in observation of a scattered light of a laser, as compared to a visual inspection, safety is obtained.

EXPLANATION OF REFERENCE NUMERALS

Figure 1:
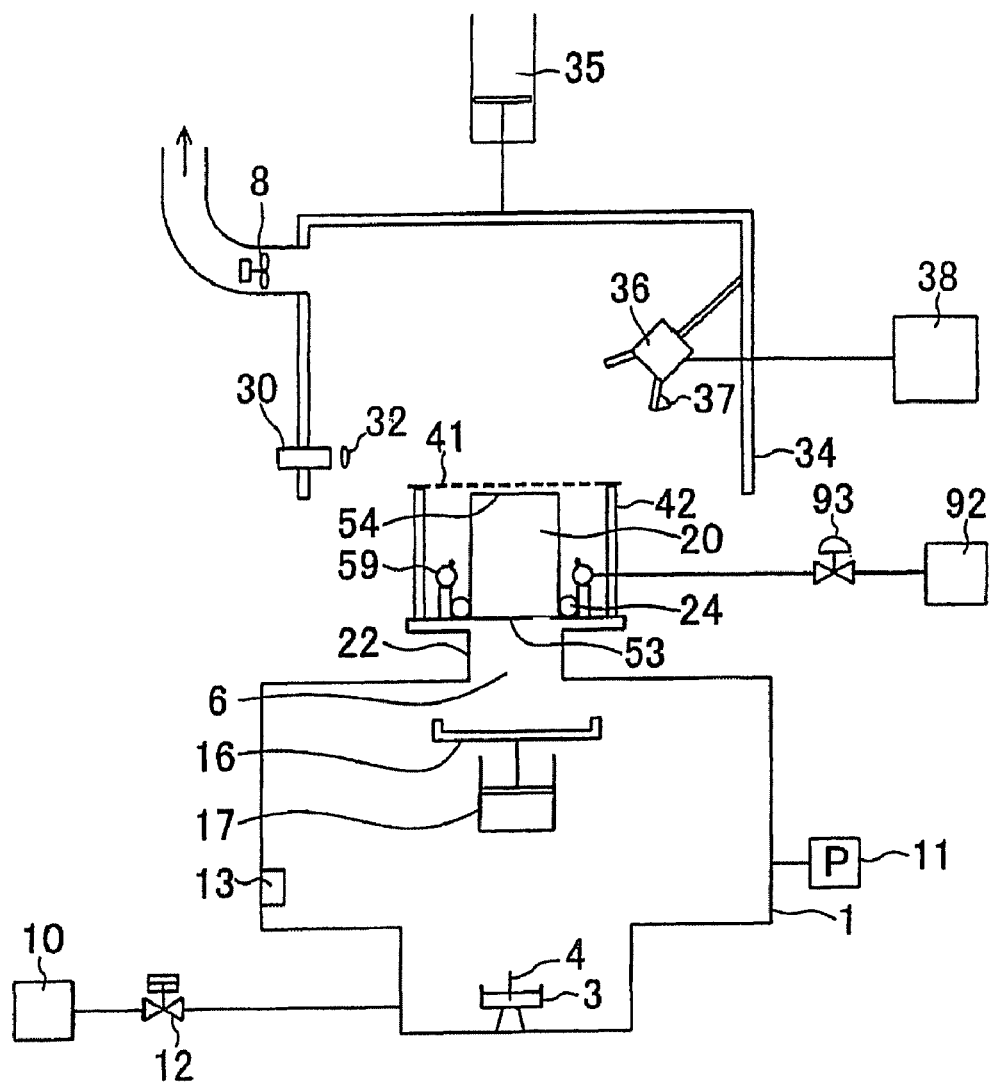
FIG. 1 is a schematic view illustrating an apparatus for inspecting defects of a honeycomb structure according to the present invention.

1: grain chamber, 3: incense stick mount, 4: incense stick, 6: fine grain inlet, 8: exhaust fan, 10: pressurization mechanism, 11: manometer, 12: fine grain introducing flow control valve, 13: fine grain densitometer, 16: fine grain inlet lid, 17: cylinder, 20: honeycomb structure, 22: platform, 24: seal, 30: light generator, 32: lens, 34: hood, 35: cylinder, 36: CCD camera, 37: air purge mechanism, 38: monitor, 41: current plate, 42: support, 51: light, 53: fine grain introduction face, 54: fine grain discharge face, 56: cell, 58: partition wall, 59: header tube, 60: plugging part, 91: nozzle, 92: air source, 93: flow control valve

DETAILED DESCRIPTION OF THE INVENTION

Hereinafter, a preferred embodiment according to the present invention will be described referring to the drawings as appropriate, but the present invention should not be interpreted to be limited to these embodiments. In the scope in which essentials according to the present invention are not impaired, based on knowledge of persons skilled in the art, various changes, modifications, improvements and substitutions can be added. For example, the drawings illustrate a preferred embodiment according to the present invention, but the present invention is not limited to the mode illustrated in the drawings or information shown in the drawings. To carry out or to examine the present invention, means similar to the one that is described in this specification or means equivalent thereto can be applied, but preferred means is means described as follows.

Figure 2:
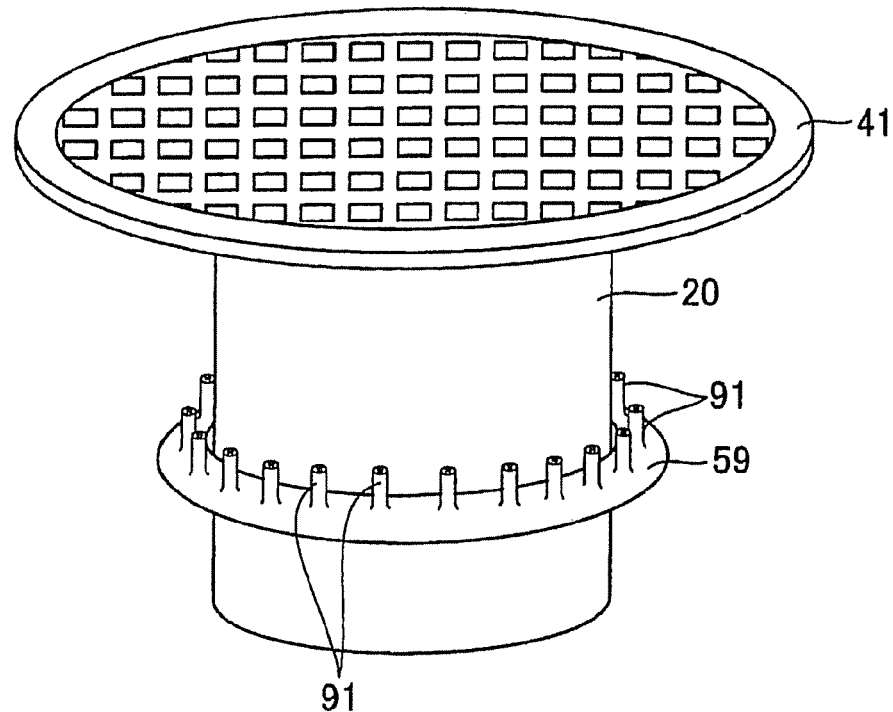
FIG. 2 is a schematic view illustrating a part of an apparatus for inspecting defects of a honeycomb structure according to the present invention.
Figure 3:
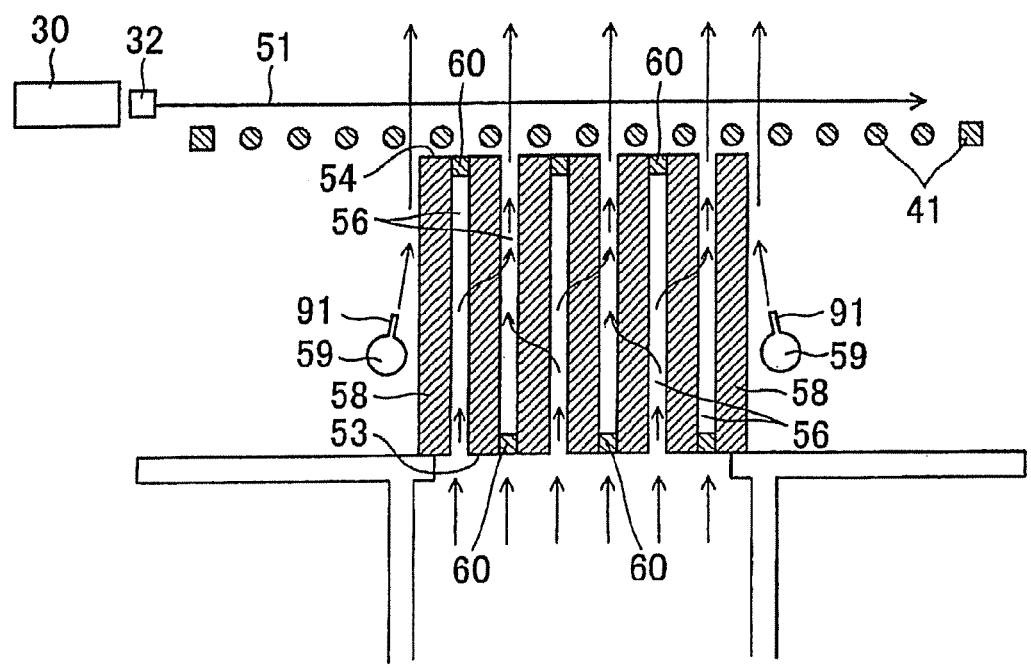
FIG. 3 is a schematic view illustrating a principle of an apparatus for inspecting defects of a honeycomb structure according to the present invention.
Figure 4:
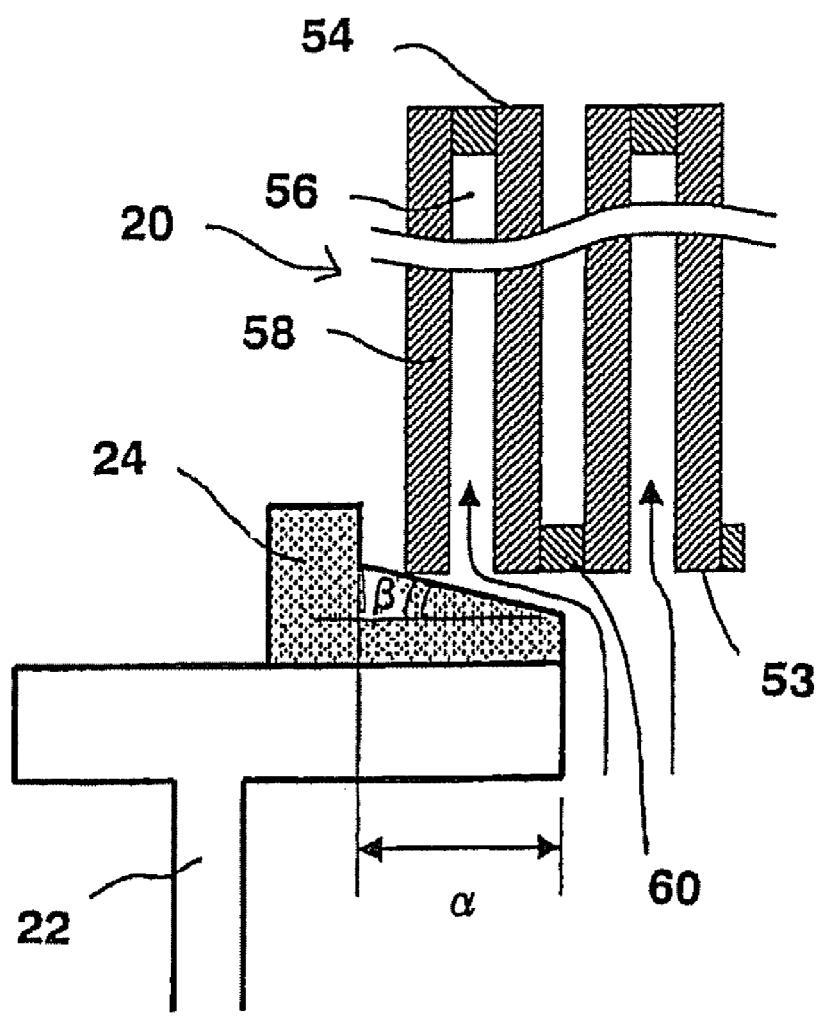
FIG. 4 is a schematic view illustrating an embodiment of an apparatus for inspecting defects of a honeycomb structure according to the present invention, and a view of illustrating a part (seal part) in an enlarged way.

FIG. 1 is a schematic view illustrating an embodiment of an apparatus for inspecting defects of a honeycomb structure according to the present invention, and a view illustrating an entire construction. FIG. 2 is a schematic view illustrating a part of an embodiment in an apparatus for inspecting defects of a honeycomb structure according to the present invention, and a perspective view illustrating a honeycomb structure (body to be inspected), a current plate and an air current formation means. FIG. 3 is a schematic view illustrating the principle of an apparatus for inspecting defects of a honeycomb structure according to the present invention, and a view illustrating the cross section of a honeycomb structure, being a body to be inspected, and illustrating the state in which a gas containing fine grains penetrate a partition wall, and a gas flows along an outer periphery of a honeycomb structure and an air current is formed. FIG. 4 is a schematic view illustrating an embodiment of an apparatus for inspecting defects of a honeycomb structure according to the present invention, and a view illustrating a part (seal part) in an enlarged manner.

First, mainly with reference to FIG. 3, the principle of an apparatus for inspecting defects of a honeycomb structure according to the present invention will be described.

A current plate 41 is disposed in the proximity of a fine grain discharge face 54 of a honeycomb structure 20, an air (gas) is blown out from a nozzle 91 of a header tube 59, an air is made to flow along the outer periphery of the honeycomb structure 20 from a fine grain introduction face 53 side to the fine grain discharge face 54 side of the honeycomb structure 20, and an air current is formed. Furthermore, a light is generated by a light generation means 30, and thus a light 51 of high directivity is applied in the proximity of the fine grain discharge face 54 through a lens 32.

In such state, when a gas containing fine grains is pressurized with respect to the honeycomb structure 20 from the fine grain introduction face 53 (from below in FIG. 3) of the honeycomb structure 20, fine grains are introduced into cells 56 that are defined by a partition wall 58 of the honeycomb structure 20, being a porous body. Further, these fine grains penetrate the partition wall 58, and are discharged from the fine grain discharge face 54. Fine grains having been discharged are directed by the current plate 41 and an air current that is formed at the outer periphery of the honeycomb structure 20, and flow a long distance in a laminar flow not to be in a turbulent flow until it reaches above the light 51 generated by the light generation means 30.

Further, fine grains having been discharged causes the light 51 to be scattered, and they themselves are visualized. Here, in the case in which there are present defects in the partition wall 58, more fine grains of larger size are discharged from the cell 56 that is defined by the partition wall 58 where these defects are present, and fine grains of larger size cause the light 51 to be scattered more. Thus, in a place where there are present larger defects, the light 51 is scattered more, thereby enabling detection of the cell 56 where there are present defects. In addition, in the case in which there are present defects at a plugging part 60, from the cell 56 that is plugged by the plugging part 60 having these defects, fine grains of larger size or more fine grains are discharged, thereby enabling detection of the cell where there are present defects.

Now, mainly with reference to FIGS. 1, 2 and 4, an apparatus for inspecting defects of a honeycomb structure according to the present invention will be described.

The apparatus for inspecting detects of a honeycomb structure according to the present invention is provided with a grain chamber 1, a platform 22, a light generator 30, a hood 34, and a CCD camera 36. In the grain chamber 1, there is stood up an incense stick 4 on an incense stick mount 3, and due to that the incense stick 4 is burned, the smoke of an incense stick is arranged to be generated. The smoke of an incense stick is fine grains with a grain diameter of about 0.3 μm to 10 μm.

At the top of the grain chamber 1, there is provided a fine grain inlet 6 of introducing fine grains from this grain chamber 1 to the honeycomb structure 20, and there are provided a pressurization mechanism 10 and a fine grain introducing flow control valve 12 in order to introduce fine grains. A gas containing fine grains residing in an internal part of the grain chamber 1 is pressurized by the pressurization mechanism 10, as well as its flow is controlled by the regulation of a pressure using the fine grain introducing flow control valve 12. Further, fine grains that are contained in this gas pass through the fine grain inlet 6 and are introduced into the honeycomb structure 20, being a body to be inspected. The preferred applied pressure is 1 Pa to 30 Pa, so that the pressurization mechanism 10 is desired to be able to apply a pressure in such a range.

There is provided in the grain chamber 1 a manometer 11 and a fine grain densitometer 13, and the pressure and the concentration of fine grains in the grain chamber 1 can be controlled. There is provided at the fine grain inlet 6 a fine grain inlet lid 16 that is connected to a cylinder 17 so that the fine grain inlet 6 can be opened or closed by the vertical motion of the cylinder 17. By the vertical motion of this cylinder 17, the fine grain inlet 6 can be opened or closed, and the fine grain inlet 6 not in use can be closed.

There is provided at the top of the fine grain inlet 6 a platform 22 having an opening in communication with the fine grain inlet 6 so that the honeycomb structure 20 can be detachably mounted. The honeycomb structure 20 is mounted on the platform 22 in the state of being sealed at the outer periphery by a seal 24. The seal 24 can take various shapes in conformity with the configuration of the honeycomb structure 20 intended to be inspected. The platform 22 is constructed in such way, so that all fine grains having passed through the fine grain inlet 6 are introduced into the honeycomb structure 20. Incidentally, the seal 24 is omitted in FIG. 3, and drawn in simplified way in FIG. 1.

There is provided above the honeycomb structure 20 a hood 34 that is connected to a cylinder 35 so as to be vertically movable, and there is provided at this hood 34 an exhaust fan 8 acting to exhaust fine grains that have been discharged from the honeycomb structure. At the time of inspection, the hood 34 is moved downward, and prevents a disturbance, for example, wind disturbing the flow of fine grains to be discharged from the honeycomb structure 20.

The light generator 30 can vertically move, and is disposed so that a light passes in the proximity right above the fine grain discharge face 54. The light is spread in a planar manner by a lens 32 and passes in parallel with the fine grain discharge face 54 of the honeycomb structure 20. Obliquely above the honeycomb structure 20, there are provided a monitor 38 and a CCD camera 36 that is connected thereto and mounted obliquely downward so as to take a photograph of a scattered light and to record it. There is provided in the proximity of the CCD camera 36 an air purge mechanism 37 that can apply a positive pressure in order to prevent the adhesion of fine grains to the camera lens.

The current plate 41 is supported by a support 42, and disposed in the proximity of the fine grain discharge face 54 of the honeycomb structure 20. The support 42 can vertically move, and thus the distance between the position of the current plate 41 and the fine grain discharge face 54 of the honeycomb structure 20 can be adjusted. A header tube 59 is connected to an air source through a piping, and in the piping, a flow control valve 93 of an air is disposed.

As described above, the seal 24 is disposed on the platform 22, and on a seat face that is formed at the seal 24, the honeycomb structure 20 is mounted. This seal 24 has a seal function with respect to the gas containing fine grains and a support function of supporting the honeycomb structure. The material of the seal 24 preferably employs resin materials, and most preferably employs materials of rubbers such as urethane rubber, silicone rubber and natural rubber.

The fine grain discharge face 54 of the honeycomb structure 20 and the current plate 41 that is disposed proximate thereto are desired to be substantially parallel. The fine grain introduction face 53 and the fine grain discharge face 54 of the honeycomb structure 20 are formed to be in parallel, so that by causing the current plate 41, the top face of the platform 22 and the seat face of the seal 24 to be in parallel, the aforementioned state in which the fine grain discharge face 54 of the honeycomb structure 20 and the current plate 41 are substantially in parallel is achieved. When the fine grain discharge face 54 of the honeycomb structure 20 and the current plate 41 are substantially in parallel, both the seal function and the support function of the seal 24 are satisfied, so that such mode (positional relationship) is one of preferred modes. When an angle which the top face of the platform 22 forms with the seat face of the seal 24 is referred to as a taper angle β, in this case, it is β=0° (refer to FIG. 4).

As described above, the seal 24 can take a variety of shapes in conformity with the shape of the fine grain introduction face 53 of the honeycomb structure 20, but, in some cases, the honeycomb structure 20 is varied in dimension even if the fine grain introduction face 53 has the same shape. In particular, at the honeycomb structure 20 that is mainly made of ceramics, there may be fluctuations at the time of formation, as well as contraction fluctuations at the time of drying and sintering. To be able to keep up with these fluctuations, the seal 24 is preferably provided with a seat face length d (refer to FIG. 4). When the range of the above-mentioned contraction fluctuations exceeds the size of one cell, there may be supposed the case of blocking the cell at the most outer peripheral portion. With respect to this case, by causing the taper angle β to be larger than zero (0), the gas containing fine grains can be introduced into the cell at the most outer peripheral portion. When, however, a taper angle β is too large, on the occasion of mounting the honeycomb structure 20, there are some cases in which the fine grain discharge face 54 of the honeycomb structure 20 and the current plate 41 cannot be held in parallel. In such cases, there is a possibility of the reduction in inspection performance of defects. Therefore, a taper angle β is preferably larger than 0 degrees and not more than 30 degrees. A taper angle β is more preferably not less than 2 degrees and not more than 15 degrees.

EXAMPLES

Hereinafter, the present invention will be specifically described based on examples, but the present invention is not limited to these examples.

Example 1

Using an apparatus for inspecting defects of a honeycomb structure illustrated in FIG. 1, defects of the honeycomb structure, being a porous body was inspected. As the honeycomb structure 20, being a body to be inspected, used was the one which is a cylindrical shape of 150 mm diameter and 150 mm length, which cell density is 40 numbers/cm$^2$, and which is plugged for use in a DPF. The current plate 41 employed the one which is a chrome-plated stainless, and which is of 100 mesh and 50 μm aperture, and it was disposed 1 mm apart from the fine grain discharge face 54 of the honeycomb structure. An air current along the outer periphery of the honeycomb structure 20 was formed by blowing out air at 6 L/min from 32 nozzles 91 formed at the header tube 59.

On the platform 22 of the apparatus for inspecting defects of a honeycomb structure illustrated in FIG. 1, the honeycomb structure was mounted using the seal 24. Further, an incense stick was burned to generate fine grains. At a point when the concentration of fine grains is 300 numbers/cc, a gas containing fine grains in the grain chamber 1 was pressurized at 10 Pa using the pressurization mechanism 10, and with the flow of the gas containing fine grains of 2 L/min, fine grains were introduced into the cells of the honeycomb structure. Using a green laser beam generator as the light generator 30, a laser light was generated via the lens 32, and the laser light was made to pass in a planar way substantially in parallel with the fine grain discharge face 54 of the honeycomb structure 5 mm above the honeycomb structure. The laser light having been scattered by discharged fine grains were photographed by the CCD camera 36, observed by the monitor 38, and recorded. Even if no after treatment was made after inspection, the function as a honeycomb structure was not impaired.

Based on recorded images, as to whether the detection of defects of the honeycomb structure 20 is easy or not, a seeing of fine defects and a seeing in the vicinity of the outer periphery were evaluated, and an overall evaluation was made as well. Results of evaluation are shown in Table 1 together with the flow of a gas containing fine grains (set value at the fine grain introducing flow control valve 12), the presence or the absence of a current plate, and the presence or the absence of the formation of an air current. In Table 1, the seeing of fine defects and the seeing in the vicinity of the outer periphery were evaluated to be o: can be clearly seen, L: in some cases, can be seen, and x: cannot be seen. The overall evaluation was made to be o: in the case in which both the seeing of fine defects and the seeing in the vicinity of the outer periphery are o, and x: in the other cases.

TABLE 1

|  | Flow (L/min) | Current plate | Air current formation | Individual evaluation | | Overall evaluation |
|---|---|---|---|---|---|---|
|  |  |  |  | Seeing of fine defects | Seeing in the vicinity of the outer periphery |  |
| Comparative Example 1 | 30 | Absent | Absent | X | Δ | X |
| Comparative Example 2 | 15 | Absent | Absent | Δ | X | X |
| Comparative Example 3 | 2 | Absent | Absent | ◯ | X | X |
| Comparative Example 4 | 2 | Present | Absent | ◯ | Δ | X |
| Example 1 | 2 | Present | Present | ◯ | ◯ | ◯ |
| Comparative Example 5 | 2 | Absent | Present | ◯ | X | X |
| Comparative Example 6 | 30 | Present | Present | X | ◯ | X |

Comparative Examples 1 to 6

Each condition of the presence or the absence of the current plate, the flow of the gas containing fine grains, and the presence or the absence of the formation of an air current was changed. With the others being the same as is Example 1, defects of the honeycomb structure 20 was inspected and it was evaluated whether or not the detection of defects of the honeycomb structure 20 is easy or not. Results of the evaluation are shown in Table 1 together with the flow of the gas containing fine grains, the presence or the absence of the current plate, and the presence or the absence of the formation of an air current.

(Examination) From results shown in Table 1, the following facts can be found. As the flow of the gas containing fine grains is decreased, the seeing of fine defects is improved and the sensitivity of detection is increased, but the seeing in the vicinity of the outer periphery is decreased (refer to Comparative Example 1 and Comparative Example 3). Although the current plate 41 provides rather enhanced effects of the seeing in the vicinity of the outer periphery, it is not sufficient (refer to Comparative Example 3 and Comparative Example 4). When there is no current plate, even if an air current is formed, the seeing in the vicinity of the outer periphery becomes rather worse (refer to Comparative Example 5). When the velocity of the gas containing fine grains is high, even if the current plate is disposed and an air current is formed, the detection sensitivity with respect to fine defects is low (refer to Comparative Example 6). By the formation of an air current, the seeing in the vicinity of the outer periphery is improved, and thus sufficient effects can be obtained (refer to Example 1).

An apparatus for inspecting defects of a honeycomb structure according to the present invention can be used as means of inspecting defects of a honeycomb structure. In particular, it is preferably used as means of inspecting defects of a DPF acting to remove granular substances from an exhaust gas.

What is claimed is:

1. An apparatus for inspecting defects of a honeycomb structure comprising:
    a fine grain introduction means for pressurizing a gas containing a fine grain to introduce the fine grain into a cell of the honeycomb structure from one face side of the honeycomb structure;
    a fine grain-containing gas flow control means for controlling a flow of the gas to be introduced;
    a light application means for applying a light of high directivity so as to pass in parallel in the vicinity of the other face of the honeycomb structure;
    a current plate disposed so as to cover the other face of the honeycomb structure between the light emitted from the light application means and the other face of the honeycomb structure; and
    an air current formation means for causing a gas to flow along an outer periphery of the honeycomb structure in a direction from one face side toward the other face side of the honeycomb structure.

2. The apparatus for inspecting defects of a honeycomb structure according to claim 1, wherein said air current formation means includes a plurality of nozzles blowing out a gas.

3. The apparatus for inspecting defects of a honeycomb structure according to claim 1, further comprising:
    an air current formation gas pressurizing means of pressurizing a gas that is made to flow by said air current formation means; and
    an air current formation gas flow control means of controlling a flow of a gas that is made to flow by said air current formation means.

4. The apparatus for inspecting defects of a honeycomb structure according to claim 1, wherein a distance between said current plate and the other face of said honeycomb structure is not less than 0.01 mm to not more than 30 mm.

5. The apparatus for inspecting defects of a honeycomb structure according to claim 1, wherein an open area of said current plate is not less than 10% to not more than 80% of a total area of said current plate.

6. The apparatus for inspecting defects of a honeycomb structure according to claim 1, wherein there is provided an observation means of observing said light scattered by said fine grain from a position forming an angle with respect to a direction of a normal to the other face of the honeycomb structure.

7. The apparatus for inspecting defects of a honeycomb structure according to claim 6, wherein said observation means is means of taking an image of the other face of said honeycomb structure using a camera.

* * * * *